US010271892B2

(12) United States Patent
Nagtegaal et al.

(10) Patent No.: US 10,271,892 B2
(45) Date of Patent: Apr. 30, 2019

(54) ELECTROSURGICAL SYSTEM (71) Applicant: GYRUS MEDICAL LIMITED, St Mellons, Cardiff (GB)

(72) Inventors: Marno Nagtegaal, Cardiff (GB); Wayne Williams, Penarth (GB); Robert Edward Taylor, Presteigne (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 519 days.

(21) Appl. No.: 14/423,585

(22) PCT Filed: Aug. 22, 2013

(86) PCT No.: PCT/GB2013/052211
§ 371 (c)(1),
(2) Date: Feb. 24, 2015

(87) PCT Pub. No.: WO2014/029999
PCT Pub. Date: Feb. 27, 2014

(65) Prior Publication Data
US 2015/0216582 A1   Aug. 6, 2015

(30) Foreign Application Priority Data

Aug. 24, 2012 (GB) .................. 1215095.9

(51) Int. Cl.
*A61B 18/14* (2006.01)
*A61B 18/04* (2006.01)
*A61B 18/00* (2006.01)

(52) U.S. Cl.
CPC .. *A61B 18/042* (2013.01); *A61B 2018/00166* (2013.01); *A61B 2018/00589* (2013.01);
(Continued)

(58) Field of Classification Search
CPC . A61B 18/042; A61B 18/1482; A61B 18/148; A61B 18/1485; A61B 18/1487;
(Continued)

(56) References Cited

U.S. PATENT DOCUMENTS 4,040,426 A   8/1977 Morrison, Jr.
5,088,997 A   2/1992 Delahuerga et al.
(Continued)

FOREIGN PATENT DOCUMENTS

WO      02/30308 A1    4/2002
WO   2008/103777 A1    8/2008
(Continued)

OTHER PUBLICATIONS

Dec. 11, 2012 Search Report issued in British Patent Application No. 1215095.9.
(Continued)

*Primary Examiner* — Thomas A Giuliani
(74) *Attorney, Agent, or Firm* — Oliff PLC (57) ABSTRACT

An electrosurgical system for the treatment of tissue includes an electrosurgical instrument, a source for supplying ionizable gas to said electrosurgical instrument, an electrosurgical generator for supplying high frequency energy to the electrosurgical instrument, and a switch mechanism. The electrosurgical instrument includes one or more conduits and one or more electrodes connected to the electrosurgical generator. The electrosurgical system is movable between at least a first and a second arrangement. The first arrangement is such that one electrode produces a stream of ionized gas exiting one of the conduits, the ionizable gas being capable of the removal of tissue. The second arrangement is such that ionized gas is produced such that it is capable of the coagulation of tissue. The
(Continued)

switch mechanism causes the electrosurgical instrument to move between the first and second arrangements.

23 Claims, 4 Drawing Sheets

(52) U.S. Cl.
CPC ............... *A61B 2018/00601* (2013.01); *A61B 2018/00958* (2013.01); *A61B 2018/1475* (2013.01)

(58) Field of Classification Search
CPC ............... A61B 18/12; A61B 18/1402; A61B 2018/00166; A61B 2018/1475; A61B 2018/00607; A61B 2018/00601; A61B 2018/00958; A61B 2018/00589; A61B 2018/1472; A61B 2018/00583; A61B 2018/00708
USPC ............... 606/32, 37, 41, 42, 45, 46, 49
See application file for complete search history.

(56) References Cited

U.S. PATENT DOCUMENTS

| | | | |
|---|---|---|---|
| 5,669,907 A | 9/1997 | Platt, Jr. et al. | |
| 6,039,736 A | 3/2000 | Platt, Jr. | |
| 6,197,026 B1 | 3/2001 | Farin et al. | |
| 6,458,125 B1 | 10/2002 | Cosmescu | |
| 6,702,812 B2 | 3/2004 | Cosmescu | |
| 2005/0043728 A1* | 2/2005 | Ciarrocca | A61B 18/1482 606/48 |
| 2009/0076505 A1* | 3/2009 | Arts | A61B 18/042 606/49 |
| 2009/0270849 A1* | 10/2009 | Truckai | A61B 18/042 606/13 |
| 2011/0118601 A1* | 5/2011 | Barnes | A61B 18/14 600/439 |
| 2012/0283732 A1 | 11/2012 | Lam | |
| 2012/0289954 A1 | 11/2012 | Lam | |

FOREIGN PATENT DOCUMENTS

| | | |
|---|---|---|
| WO | 2011055368 A2 | 5/2011 |
| WO | 2011055369 A2 | 5/2011 |
| WO | 2012061535 A2 | 5/2012 |

OTHER PUBLICATIONS

Dec. 11, 2013 International Search Report issued in International Patent Application No. PCT/GB2013/052211.

Dec. 11, 2013 Written Opinion issued in International Patent Application No. PCT/GB2013/052211.

\* cited by examiner

ELECTROSURGICAL SYSTEM

TECHNICAL FIELD

This invention relates to an electrosurgical system and in particular to the non-contact treatment of tissue using an ionisable gas such as argon.

BACKGROUND TO THE INVENTION

Argon beam coagulators have been known for many years, and examples are given in U.S. Pat. Nos. 4,040,426, 6,039,736 and 6,197,026. The first example is an end-effect instrument, in which the ionised gas exits through the end of the instrument, while the latter two examples are directed at side-effect instruments, in which the ionised gas exits the instrument though an aperture in the side of the instrument. Such instruments are often referred to as APC instruments (Argon Plasma Coagulation).

The majority of these instruments perform purely tissue coagulation and have no tissue cutting capability. Where such instruments do have a tissue cutting capability, this is achieved by a tissue contacting needle or other electrode. Examples are U.S. Pat. Nos. 5,088,997 and 6,702,812, which both provide a forwardly extending tissue-contacting electrode to perform the cutting of tissue.

SUMMARY OF THE INVENTION

Embodiments of the invention provide an instrument which is more versatile than any of the instruments in the prior art, and in particular provides for selecting between non-contact tissue coagulation and non-contact tissue removal. Accordingly, an electrosurgical system is provided for the treatment of tissue, the system comprising an electrosurgical instrument, a source for supplying ionisable gas to said electrosurgical instrument, an electrosurgical generator for supplying high frequency energy to said electrosurgical instrument, and a switch mechanism, the electrosurgical instrument including at least one elongated shaft having a proximal end and a distal end, and including at least one conduit though which ionisable gas can be supplied to the distal end of the shaft, the shaft including at least one aperture located at the distal end thereof, and at least one electrode for ionising the ionisable gas exiting the at least one aperture, the electrosurgical instrument being movable between at least a first and a second arrangement, the first arrangement being such that the at least one electrode produces a stream of ionised gas exiting the at least one aperture of such energy that it is capable of the removal of the tissue being treated, and the second arrangement being such that the at least one electrode produces a stream of ionised gas exiting the at least one aperture capable of the coagulation of the tissue being treated, the operation of the switch mechanism causing the electrosurgical instrument to switch between the first and second arrangements.

In this way, the electrosurgical instrument is capable of switching between the first arrangement, which provides non-contact removal of tissue, and the second arrangement, which provides for tissue coagulation. By the term tissue removal, there is herein meant to include the volumetric removal of tissue by means of tissue vaporisation, or tissue dissection by means of removal of a line of tissue between two previously connected sections of tissue. Conveniently, the electrosurgical instrument comprises first and second electrodes, and therefore acts as a bipolar electrosurgical instrument.

According to a convenient arrangement, the electrosurgical instrument includes first and second conduits. Typically, the first electrode is associated with the first conduit, and the second electrode is associated with the second conduit. The first and second conduits are preferably disposed parallel to one another along a common longitudinal axis.

U.S. Pat. No. 5,669,907 describes an argon coagulation instrument incorporating two tubes with an electrode in each tube. However, U.S. Pat. No. 5,669,907 provides only tissue coagulation and has no tissue-cutting capability whatsoever. Other prior systems, such as those described in US2009/0270849 and WO02/30308, attempt to provide tissue coagulation and tissue cutting merely by changing the power of the energy supplied to the tissue. In contrast, the present invention can be switched between this tissue coagulating mode and a non-contact tissue removal capability by a small movement of the instrument, ensuring that both actions can be optimally provided from a single instrument.

Conveniently, the first and second conduits are separated by an electrically insulating divider. This divider, which can take the form of a ceramic or quartz shield, ensures that in the tissue coagulating mode, the strength of the dielectric between the two electrodes means that the stream of ionised gas is forced to take an extended route between the first and second electrodes.

The source is preferably capable of selectively supplying ionisable gas to one or both conduits. In the first arrangement, the source conveniently supplies ionised gas solely to the first conduit. This ensures that the ionised gas stream emerging from the first conduit is directed at the tissue as opposed to being attracted to the second electrode. In the second arrangement, the source supplies ionised gas to both the first and second conduits. In this second arrangement, the presence of gas emerging from both conduits means that the stream of ionised gas passes not from the first electrode to the tissue, but from the first electrode to the second electrode. This causes a stream of ionised gas in the form of a "loop", which creates sufficient heat adjacent the distal tip of the instrument to cause the coagulation of any tissue brought into the general proximity of the tip of the instrument.

According to a further convenient arrangement, the movement of the electrosurgical instrument between the two arrangements is conveniently constituted by moving one of the first and second electrodes relative to the other electrode between two positions, a first position in which one electrode is longitudinally set back from the other electrode, and a second position in which the two electrodes are substantially at the same longitudinal position with respect to each other. In the first position, with one electrode longitudinally set back from the other, the ionised gas stream emerging from the first conduit is directed at the tissue as opposed to being attracted to the second electrode. This conveniently constitutes the first arrangement as described previously, for the removal of tissue. Conversely, in the second position, with both electrodes adjacent one another at the same longitudinal location, the stream of ionised gas passes from the first electrode to the second electrode. This conveniently constitutes the second arrangement as described previously, for the coagulation of tissue.

In one convenient construction, in which the first and second tubes are provided, the movement of the instrument between the two arrangements is conveniently constituted by moving the first and second tubes longitudinally relative to one another between a first position in which the first elongated tube is distal of the second elongated tube, and a second position in which the first and second elongated tubes are adjacent one another. In the first position, the electrically insulating divider is typically substantially adjacent the first elongated tube. In the second position, the electrically insulating divider is typically distal of both the first and second elongated tubes. In this way, when the stream of ionised gas passes from the first electrode to the second electrode, it is forced to take an extended route around the insulating divider, thereby creating a larger area of heat-generating plasma capable of coagulating tissue in tits general proximity. This means that the electrosurgical system is capable of providing non-contact tissue removal or tissue coagulation at will, merely by the operation of the switch mechanism.

Alternatively, the first and second conduits are comprised by first and second tubes coaxially disposed one inside the other. Conveniently, the second tube is coaxially disposed inside the first tube, the second tube being longitudinally movable with respect to the first tube between first and second positions. In the first position, the second tube is typically at substantially the same longitudinal position with respect to the first tube, whereas in the second position, the second tube is typically withdrawn into a longitudinally set back position as compared with the longitudinal position of the first tube.

When the second tube is in its first position, the aperture for gas to flow from the end of the instrument is solely provided by the lumen within the second tube, as the lumen within the first tube is entirely taken up by the second tube. This means that the gas outflow aperture is relatively narrow, and suitable for the instrument to be operated in a manner capable of cutting tissue. So, when the instrument is desired to be operated for tissue cutting in its first arrangement, the second tube is moved to the first position, such that the gas outflow aperture is relatively narrow.

Conversely, when the second tube is in its second position, the aperture for gas flow from the end of the instrument is provided by the lumen within the first tube, as the second tube is withdrawn at least partially within the first tube. This means that the gas outflow aperture is wider, and suitable for the instrument to be operated in a manner capable of the non-contact coagulation of tissue. Therefore, when the instrument is desired to be operated for tissue coagulation in its second arrangement, the second tube is moved to the second position, such that the gas outflow aperture is relatively wide and suitable for coagulation.

In view of the above, generally in the first arrangement a first effective aperture through which the stream of ionised gas exits is smaller than a second effective aperture through which the gas exits in the second arrangement. Therefore, with the smaller aperture a more focused gas stream is obtained which constrains the high frequency energy in a smaller area and hence produces a cutting action. Conversely, with the larger aperture of the second arrangement the high frequency energy is spread across a greater volume of ionised gas, and hence produces a coagulation or desiccation effect.

The first and second effective apertures can be obtained in a variety of ways. In one embodiment an elongated shaft includes first and second conduits, wherein in the first arrangement the stream of ionised gas exits through the first conduit constituting the first effective aperture and not the second conduit, and in the second arrangement the ionised gas exits through both the first and second conduits collectively constituting the second effective aperture.

Alternatively, in another embodiment an elongated shaft is provided including a gas conduit having the at least one aperture at a distal end thereof, the gas conduit being arranged to allow for widening of the at least one aperture from a first width that provides the first effective aperture, to a second width that provides the second effective aperture. Within this embodiment preferably the gas conduit comprises an inner tube and an outer tube concentrically arranged, the inner tube being movable within the outer tube, the first effective aperture being provided by a distal aperture of the inner tube when the distal aperture of the inner tube is aligned or extends beyond a distal aperture of the outer tube, and the second effective aperture being provided by the distal aperture of the outer tube when the inner tube is slidably moved such that the distal aperture thereof is located within the outer tube spatially separated from the distal end of the outer tube. Such an arrangement provides a compact and reliable instrument.

From another aspect embodiments of the invention also provide a method of operating an electrosurgical system for the treatment of tissue, comprising: a) supplying ionisable gas to an electrosurgical instrument, the electrosurgical instrument including at least one elongated shaft having a proximal end and a distal end, and including at least one conduit though which the ionisable gas is supplied to the distal end of the shaft, the shaft including at least one aperture located at the distal end thereof, and at least one electrode for ionising the ionisable gas exiting the at least one aperture; b) supplying high frequency energy to said at least one electrode from a high frequency generator to ionise the ionisable gas; and c) moving the electrosurgical instrument between at least a first and a second arrangement, the first arrangement being such that the at least one electrode produces a stream of ionised gas exiting the at least one aperture of such energy that it is capable of the removal of the tissue being treated, and the second arrangement being such that the at least one electrode produces a stream of ionised gas exiting the at least one aperture capable of the coagulation of the tissue being treated.

BRIEF DESCRIPTION OF THE DRAWINGS

Embodiments of the invention will now be further described, by way of example only, with reference to the accompanying drawings, in which.

DESCRIPTION OF THE EMBODIMENTS

Figure 1:
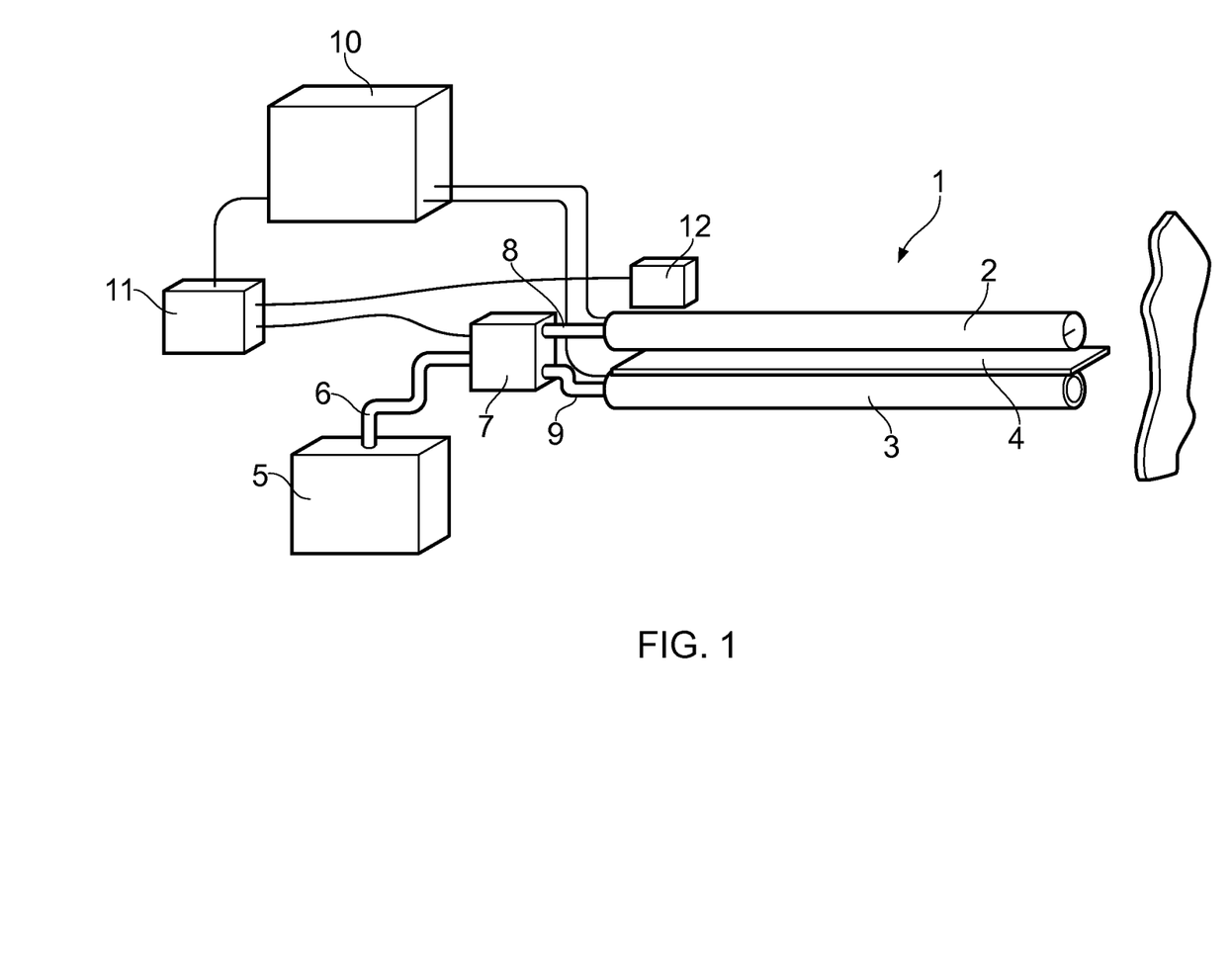
FIG. 1 is a schematic view of an electrosurgical system in accordance with the present invention.

Referring to FIG. 1, an electrosurgical system comprises an instrument shown generally at 1, consisting of a first tube 2 and a second tube 3, situated parallel to one another and separated by a ceramic divider 4. Argon gas is supplied to each tube from a reservoir 5, via a pipe 6 and a flow valve 7. The flow valve directs the argon gas to one or both of tubes 2 & 3, via pipes 8 & 9. An electrosurgical generator 10 provides RF energy to electrodes mounted on each tube, to be described in more detail later. A switch mechanism 11 send signals to control the electrosurgical generator 10 and also the flow valve 7, as well as a servo motor 12 the function of which will also be described in more detail later.

Figure 2:
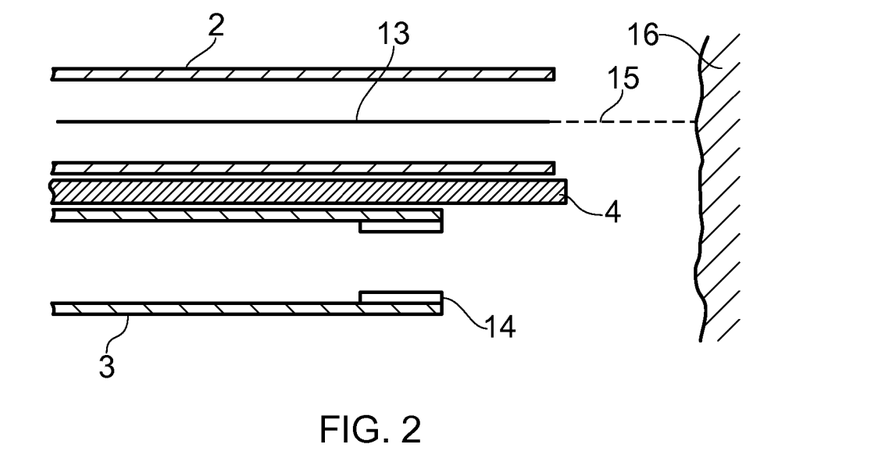
FIG. 2 is a sectional side view of the tip of an electrosurgical instrument used as part of the electrosurgical system of FIG. 1, shown in a first configuration.

FIG. 2 shows the distal end of the tubes 2 & 3 in a first arrangement suitable for tissue removal. The servo motor has moved the first tube 2 forwardly, so that it is in advance of the second tube 3. A central tungsten electrode 13 is provided coaxially within the first tube 2, and connected to one pole of the electrosurgical generator 10. A cylindrical return electrode 14 is present at the end of the second tube 3, and is connected to the opposite pole of the electrosurgical generator 10.

When the user of the instrument 1 intends to cut tissue, the switch mechanism 11 is operated to instruct the servo motor 12 to move the first tube 2 into the position shown in FIG. 2. The switch mechanism also instructs the flow valve 7 to supply argon gas to the first tube 2 through pipe 8, but to block the flow of argon gas to second tube 3 through pipe 9. In this way, argon gas is only flowing from the distal end of the first tube 2. The switch mechanism also instructs the electrosurgical generator 10 to supply a high voltage RF signal to the electrode 13. This causes the argon gas flowing past the electrode 13 to be ionised into a stream of plasma 15 which flows forwardly from the end of the first tube in the form of a concentrated beam. The plasma stream 15 strikes tissue 16 in front of the tube 2, causing tissue removal due to the high temperature of the plasma 15. The cylindrical return electrode 14 present on the second tube 3 is not in contact with the tissue 16, and the electric circuit is completed by a capacitive coupling between the tissue 16 and the electrode 14, through the dielectric material of the air gap therebetween.

Figure 3:
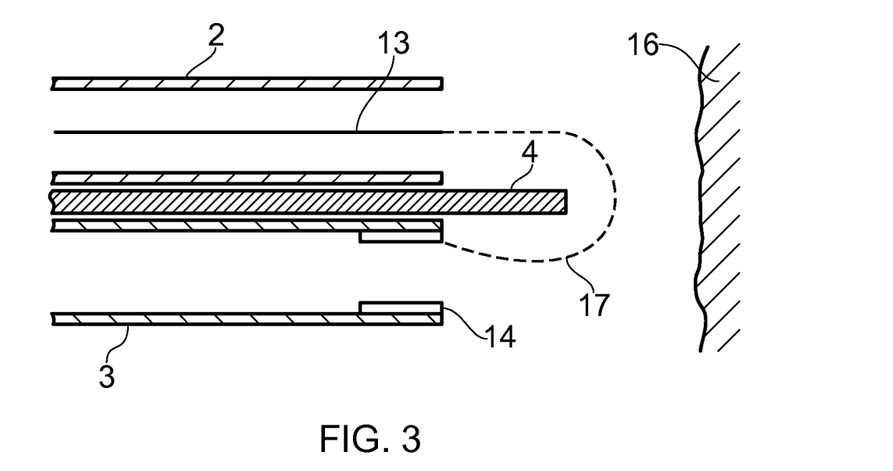
FIG. 3 is a sectional side view of the tip of the electrosurgical instrument of FIG. 2, shown in a second configuration.

When the user of the instrument 1 intends to coagulate tissue, a different setting of the switch mechanism 11 is selected which causes the servo motor 12 to move the first tube into the position shown in FIG. 3. In this position, the first and second tubes 2 & 3 are level one with another, with the ceramic divider 4 extending distally of both tubes. The switch mechanism also instructs the flow valve 7 to supply argon gas to both the first tube 2 (through pipe 8), and also to the second tube 3 (through pipe 9). As before, when the electrosurgical generator 10 supplies a high voltage RF signal to the electrode 13, the argon gas flowing past the electrode 13 is ionised into a stream of plasma. However, now there is also argon gas flowing from the second tube 3, and this causes the plasma stream to form a loop 17 between the electrodes 13 & 14. The presence of the ceramic divider 4 between the two tubes 2 & 3 ensures that the loop 17 is of a sufficient length so as to generate a large heat source such that the tissue 16 in the vicinity of the loop becomes coagulated.

The combination of the switch mechanism 11, the flow valve 7 and the servo motor 12 means that the user of the instrument 1 is able to change between the first arrangement of FIG. 2 and the second arrangement of FIG. 3 at will, without withdrawing the instrument from the surgical site. In this way, tissue removal and coagulation are both available, from the same instrument, whenever required.

Figure 4:
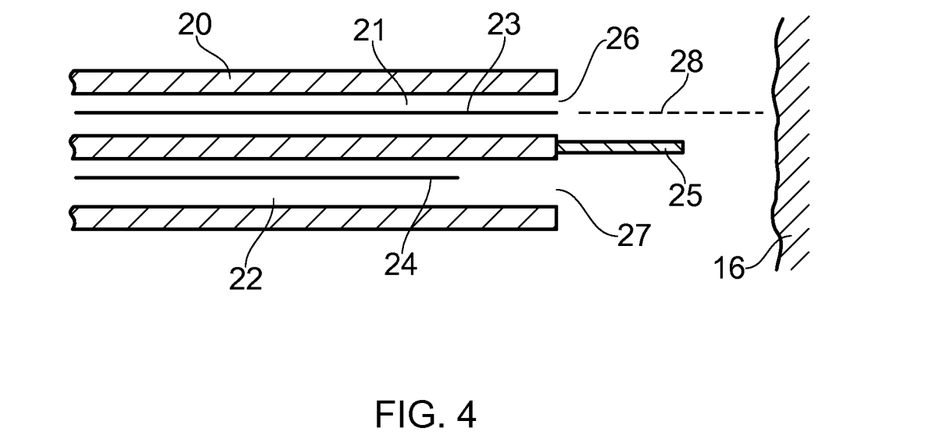
FIG. 4 is a sectional side view of the tip of an electrosurgical instrument according to an alternative embodiment of the present invention.

FIG. 4 shows an alternative embodiment, in which instead of the two tubes 2 & 3 of FIGS. 1 to 3, the instrument comprises a single solid shaft 20 with two parallel lumens 21 and 22 running the length thereof. A first electrode 23 is present within the first lumen 21, while a second electrode 24 is present within the second lumen 22. A ceramic divider 25 extends from the end of the shaft 20 situated between the openings 26 & 27 of each of the lumens.

In FIG. 4, the second electrode 24 is shown in a position in which it has been withdrawn such that it is axially set back with respect to the first electrode 23. This means that when argon gas flowing past the first electrode 23 is ionised into a stream of plasma, the plasma 28 flows forwardly from the shaft 20 to impinge on the tissue 16 in the form of a concentrated beam, removing tissue from the area where the plasma 28 strikes the tissue.

Figure 5:
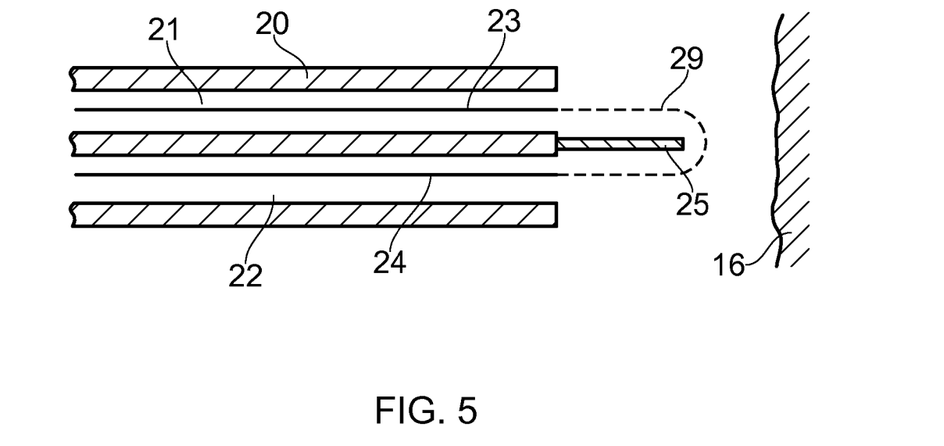
FIG. 5 is a sectional side view of the tip of the instrument of FIG. 4, shown in a second configuration.

FIG. 5 shows the instrument of FIG. 4 in an alternative configuration, in which the second electrode 24 is advanced so that it is level with the first electrode 23. In this arrangement, argon gas is directed down both lumens 21 and 22, such that when the gas is ionised into a plasma by the first electrode 23, the plasma flows in a loop 29 around the ceramic divider 25 to the second electrode 24. The plasma loop 29 is of a sufficient length so as to generate a large heat source such that the tissue 16 in the vicinity of the loop becomes coagulated.

Figure 6:
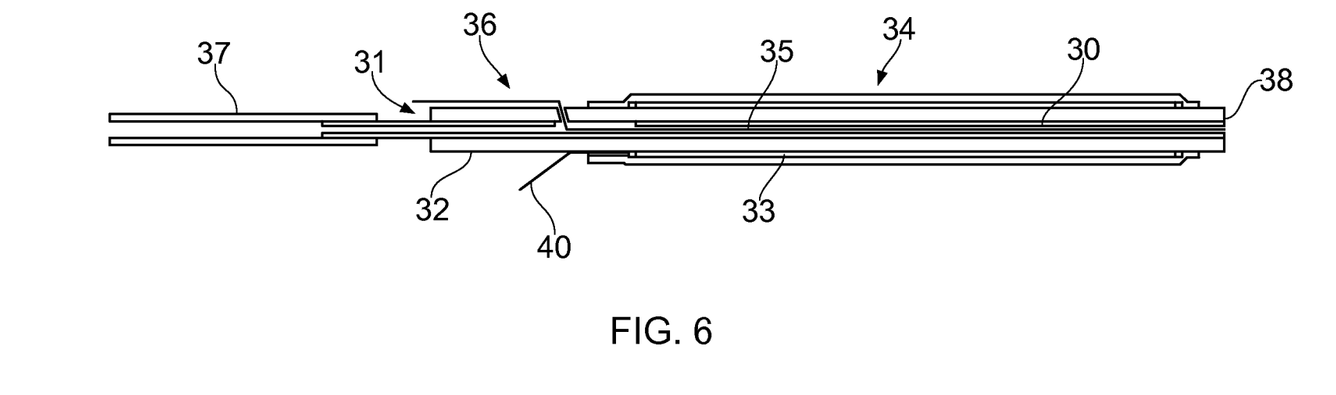
FIG. 6 is a sectional side view of the tip of an electrosurgical instrument according to an alternative embodiment of the present invention.

FIG. 6 shows a further alternative embodiment, in which two concentric tubes are employed instead of the side-by-side tubes of FIGS. 1 to 3. A ceramic inner tube 30 is slideably disposed within the lumen 31 of a stationary ceramic outer tube 32. The outer tube 32 is housed in a stainless steel tube 33, which is itself surrounded by an insulating sleeve 34. The inner tube 30 is also provided with a central lumen 35, along which runs an electrode wire 36. The inner tube 30 is connected at its proximal end to a gas supply tube 37. The stainless steel tube 33 acts as a return electrode for the electrode wire 36, being connected to the generator 10 by means of lead 40.

In FIG. 6, the inner tube 30 is in its first position, in which it is flush with the end of the outer tube 32 such that the gas flows past the end of the electrode wire 36, and out from the distal end 38 of the instrument through the lumen 35. The gas is ionised into a stream of plasma by the electrode wire 36, and as the lumen 35 is relatively narrow, the stream of plasma flows forwardly from the distal end 38 of the instrument in the form of a concentrated beam, capable of tissue removal.

Figure 7:
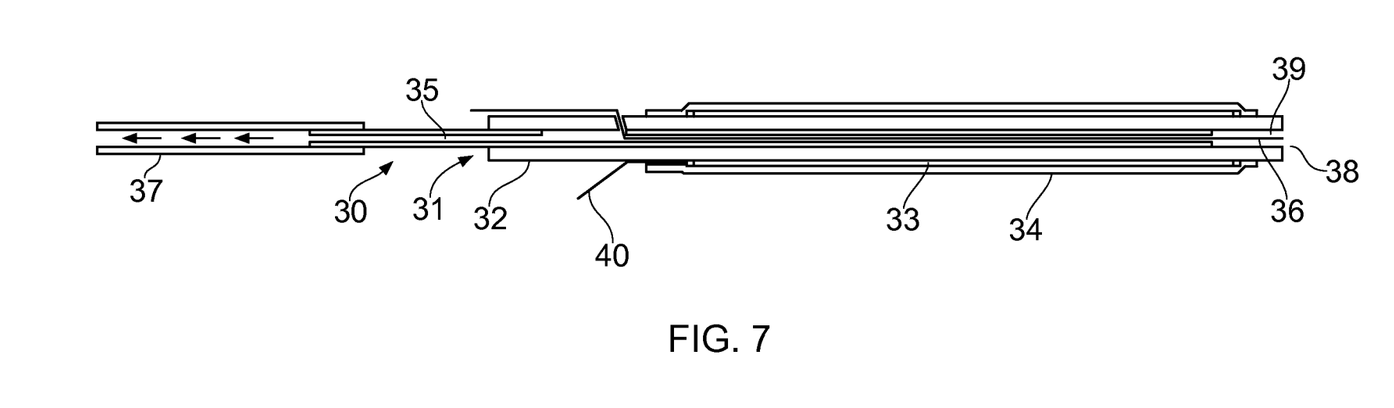
FIG. 7 is a sectional side view of the tip of the instrument of FIG. 6, shown in a second configuration.

FIG. 7 shows the instrument moved into its second position, in which the inner tube 30 has been withdrawn within the outer tube 32 to form a wider chamber 39 at the distal end 38 of the instrument. In this second position, gas flows into the chamber 39 and is ionised by the electrode wire 36, but instead of flowing from the end of the instrument as a concentrated beam, the plasma emerges as a diverging cloud, due to the larger aperture size created by the chamber 39. In the configuration of FIG. 7, the diverging plasma is capable of the broad coagulation of tissue rather than tissue removal.

Whichever arrangement is employed, the instrument is able to be operated selectively in either mode of operation, producing either the concentrated beam of plasma to perform the volumetric removal of tissue, or a more diverging plasma which generates sufficient heat to perform the coagulation of tissue. Either mode can be selected by the user of the system, without withdrawing the instrument from the surgical site, such that tissue removal and coagulation can be performed in a non-contact manner with the same instrument.

The invention claimed is:

1. An electrosurgical system for the treatment of tissue, comprising an electrosurgical instrument, a source for supplying ionisable gas to said electrosurgical instrument, an electrosurgical generator for supplying high frequency energy to said electrosurgical instrument, and a switch mechanism, the electrosurgical instrument including first and second tubes each having a proximal end and a distal-most end though which ionisable gas is configured to pass, the first and second tubes each including:
at least one aperture located at the distal-most end thereof such that ionisable gas can flow out of the distal-most end of the first and second tubes, and
an electrode for ionising the ionisable gas exiting the at least one aperture,
wherein:
one of the first and second tubes is a moveable tube that is longitudinally movable relative to the other tube between at least a first position and a second position,
movement of the moveable tube to the first position causes the instrument to assume a first arrangement in which the instrument produces a stream of ionised gas that flows only out of the distal-most end of the first tube with such energy that the stream is capable of removal of the tissue being treated,
movement of the moveable tube to the second position causes the instrument to assume a second arrangement in which the instrument produces a stream of ionised gas that flows out of the distal-most end of the first and second tubes and is capable of coagulation of the tissue being treated, and
operation of the switch mechanism causes the moveable tube to move between the first position and the second position.

2. The electrosurgical system according to claim 1, wherein the first and second tubes are disposed parallel to one another along a common longitudinal axis.

3. The electrosurgical system according to claim 2, wherein the first and second tubes are arranged such that the first tube is distal of the second tube when the moveable tube is in the first position, and the first and second tubes are adjacent one another when the moveable tube is in the second position.

4. The electrosurgical system according to claim 1, wherein the source is capable of selectively supplying ionisable gas to one or both of the first and second tubes.

5. The electrosurgical system according to claim 4, wherein in the first arrangement, the source supplies ionised gas solely to the first tube.

6. The electrosurgical system according to claim 4, wherein in the second arrangement, the source supplies ionised gas to both the first and second tubes.

7. The electrosurgical system according to claim 1, further comprising an electrically insulating divider between the first and second tubes.

8. The electrosurgical system according to claim 7, wherein, in the first position, the electrically insulating divider is substantially adjacent the first tube.

9. The electrosurgical system according to claim 8, wherein in the second position, the electrically insulating divider is distal of both the first and second tubes.

10. A method of operating an electrosurgical system for the treatment of tissue, comprising:
a) providing the electrosurgical system according to claim 1;
b) supplying ionisable gas to the electrosurgical instrument;
c) supplying high frequency energy to the electrode from the high frequency generator to ionise the ionisable gas; and
d) producing a stream of ionised gas to remove tissue when the moveable tube is in the first position, and/or producing a stream of ionised gas to coagulate tissue when the moveable tube is in the second position.

11. An electrosurgical system for the treatment of tissue, comprising an electrosurgical instrument, a source for supplying ionisable gas to said electrosurgical instrument, an electrosurgical generator for supplying high frequency energy to said electrosurgical instrument, and a switch mechanism, the electrosurgical instrument including first and second tubes each having a proximal end and a distal-most end though which ionisable gas is configured to pass, the first and second tubes each including:
at least one aperture located at the distal-most end thereof such that ionisable gas can flow out of the distal-most end of the first and second tubes, and
an electrode for ionising the ionisable gas exiting the at least one aperture,
wherein:
one of the electrodes is a moveable electrode that is longitudinally movable within its respective tube between at least a first position and a second position,
movement of the moveable electrode to the first position causes the instrument to assume a first arrangement in which the instrument produces a stream of ionised gas that flows only out of the distal-most end of the first tube with such energy that the stream is capable of removal of the tissue being treated,
movement of the moveable electrode to the second position causes the instrument to assume a second arrangement in which the instrument produces a stream of ionised gas that flows out of the distal-most end of the first and second tubes and is capable of coagulation of the tissue being treated, and
operation of the switch mechanism causes the movable electrode to move between the first position and the second position.

12. The electrosurgical system according to claim 11, wherein the first and second tubes are disposed parallel to one another along a common longitudinal axis.

13. The electrosurgical system according to claim 12, wherein the moveable electrode is longitudinally set back from the other electrode in the first position, and the two electrodes are substantially at the same longitudinal position with respect to each other when the moveable electrode is in the second position.

14. The electrosurgical system according to claim 11, wherein the source is capable of selectively supplying ionisable gas to one or both tubes.

15. The electrosurgical system according to claim 14, wherein in the first arrangement, the source supplies ionised gas solely to the first tube.

16. The electrosurgical system according to claim 14, wherein in the second arrangement, the source supplies ionised gas to both the first and second tubes.

17. The electrosurgical system according to claim 11, further comprising an electrically insulating divider between the first and second tubes.

18. The electrosurgical system according to claim 17, wherein in both the first and second positions, the electrically insulating divider is distal of both the first and second tubes.

19. A method of operating an electrosurgical system for the treatment of tissue, comprising:
   a) providing the electrosurgical system according to claim 11;
   b) supplying ionisable gas to the electrosurgical instrument;
   c) supplying high frequency energy to the electrode from the high frequency generator to ionise the ionisable gas; and
   d) producing a stream of ionised gas to remove tissue when the moveable electrode is in the first position, and/or producing a stream of ionised gas to coagulate tissue when the moveable electrode is in the second position.

20. An electrosurgical system for the treatment of tissue, comprising an electrosurgical instrument, a source for supplying ionisable gas to said electrosurgical instrument, an electrosurgical generator for supplying high frequency energy to said electrosurgical instrument, and a switch mechanism,
   the electrosurgical instrument including inner and outer tubes coaxially disposed one inside the other and each having a proximal end and a distal-most end though which ionisable gas is configured to pass, the inner and outer tubes each including:
      at least one aperture located at the distal-most end thereof such that ionisable gas can flow out of the distal-most end of the inner and outer tubes, and
      at least one electrode for ionising the ionisable gas exiting the at least one aperture,
   wherein:
      the inner tube is longitudinally movable within the outer tube between at least a first position and a second position,
      movement of the inner tube to the first position causes the instrument to assume a first arrangement in which the instrument produces a stream of ionised gas that flows only out of the distal-most end of the inner tube with such energy that the stream is capable of removal of the tissue being treated,
      movement of the inner tube to the second position causes the instrument to assume a second arrangement in which the instrument produces a stream of ionised gas that flows out of the distal-most end of the outer tube and is capable of coagulation of the tissue being treated, and
      operation of the switch mechanism causes the inner tube to move between the first position and the second position.

21. The electrosurgical system according to claim 20, wherein in the first position, the inner tube is at substantially the same longitudinal position with respect to the outer tube.

22. The electrosurgical system according to claim 21, wherein in the second position, the inner tube is withdrawn into a longitudinally set back position as compared with the longitudinal position of the outer tube.

23. A method of operating an electrosurgical system for the treatment of tissue, comprising:
   a) providing the electrosurgical system according to claim 20;
   b) supplying ionisable gas to the electrosurgical instrument;
   c) supplying high frequency energy to the electrode from the high frequency generator to ionise the ionisable gas; and
   d) producing a stream of ionised gas to remove tissue when the inner tube is in the first position, and/or producing a stream of ionised gas to coagulate tissue when the inner tube is in the second position.

* * * * *